US00PP15995P3

(12) United States Plant Patent
Eremin

(10) Patent No.: US PP15,995 P3
(45) Date of Patent: Sep. 27, 2005

(54) ***PRUNUS* PLANT NAMED 'VVA-1'**

(50) Latin Name: ***Prunus tomentosa*×*Prunus cerasifera***
Varietal Denomination: VVA-1

(75) Inventor: Guennadi Eremin, Krymsk (RU)

(73) Assignee: Varieties International, LLC, Dundee, OR (US)

( * ) Notice: Subject to any disclaimer, the term of this patent is extended or adjusted under 35 U.S.C. 154(b) by 358 days.

(21) Appl. No.: 09/880,952

(22) Filed: Jan. 11, 2002

(65) Prior Publication Data

US 2003/0233691 P1 Dec. 18, 2003

(51) Int. Cl.[7] ..... A01H 5/00
(52) U.S. Cl. ..... Plt./183
(58) Field of Search ..... Plt./183

(56) References Cited

U.S. PATENT DOCUMENTS

PP14,126 P3 * 9/2003 Zaiger et al. ..... Plt./183
2003/0208807 P1 * 11/2003 Wolfram ..... Plt./183

OTHER PUBLICATIONS

UPOV ROM GTITM Computer Database, GTI JOUVE Retrieval Software 2003/05 citations for 'VVA–1'.*

Provorchenko et al., Intensive Orchards of Stone Fruits on VVA–1 Rootstock. Sadovodstvo i Vinogradarstvo (No. 2) p. 4–5 1996.*

* cited by examiner

*Primary Examiner*—Kent L. Bell
*Assistant Examiner*—W. C. Haas
(74) *Attorney, Agent, or Firm*—Webb Ziesenheim Logsdon Orkin & Hanson P.C.

(57) ABSTRACT

A new and distinct rootstock variety of *Prunus* named 'VVA-1' that is characterized by a dwarf habit, resistance to low temperatures, the ability to serve well as rootstock that is compatible with other crops, and the ability to propagate well. In combination these traits set the new cultivar apart from all other existing varieties of *Prunus* rootstock.

1 Drawing Sheet

Botanical classification: *Prunus tomentosa*×*Prunus cerasifera*.
Varietal denomination: 'VVA-1'.

CROSS-REFERENCE TO RELATED APPLICATIONS

The application for the new invention *Prunus* Plant Named 'VVA-1' is co-pending with three other U.S. Plant Patent Applications: *Prunus* Plant Named 'VSV-1' (U.S. Plant patent application Ser. No. 09/880,951), *Prunus* Plant Named 'VSL-2' (U.S. Plant patent application Ser. No. 09/880,953), and *Prunus* Plant Named 'LC-52' (U.S. Plant patent application Ser. No. 09/880,950), each having the same filing date and inventor.

BACKGROUND OF THE INVENTION

The present invention relates to the new and distinct cultivar known botanically as a hybrid of *Prunus* and referred to hereinafter as 'VVA-1'. The new invention was bred by the inventor at the Breeding Station in Krymsk, Russia.

The breeding program at the Breeding Station was established in 1956 and funded by the government of the former Soviet Union for the purpose of producing new improved *Prunus* cultivars that serve well as rootstock, are dwarf in size, resistant to low temperatures, compatible with peach, plum and apricot, and propagate well by use of hardwood, softwood cuttings, and meristem cuttings in vitro.

The inventor obtained seed from the female parent *Prunus tomentosa* (not patented), in his own garden in Moscow and planted the seed in a cultivated area of Krymsk, Russia. The resulting seedlings were then planted in a *Prunus cerasifera* (not patented) orchard during blossom time. Here the seedlings were pollinated by the male parent *Prunus cerasifera*. The resulting seeds were sown and the new cultivar 'VVA-1' was selected from these seedlings in 1966. Ten years of observation and evaluation followed at the Breeding Station in Krymsk, Russia. The new cultivar originated as a single plant and is the result of a hybrid cross between the female parent *Prunus tomentosa* (not patented) and the male parent *Prunus cerasifera* (not patented).

The closest comparison plant is the female parent *Prunus tomentosa*. 'VVA-1' differs from the female parent in its long leaf, large and dark fruit and low fruit bearing. The characteristics that distinguish the new cultivar from the male parent are dwarf habit, wrinkled leaf, and pubescent stems. The distinguishing traits that make 'VVA-1' unique from all other existing varieties of *Prunus* rootstock known to the inventor include resistance to low temperatures, dwarf habit, ability to serve as rootstock that is compatible with other crops, and the ability to propagate well by use of hardwood, softwood cuttings and meristem cuttings in vitro.

'VVA-1' was first asexually propagated in 1966 by the inventor at the Breeding Station in Krymsk, Russia. The method used was softwood cuttings. The distinguishing traits have been determined stable and are reproduced true to type in successive generations.

SUMMARY OF THE INVENTION

The following traits have been repeatedly observed and represent the distinguishing characteristics of the new cultivar. These traits in combination distinguish 'VVA-1' from all other existing cultivars of *Prunus* hybrid rootstock known to the inventor. 'VVA-1' has not been tested under all possible conditions and phenotypic differences may be observed with variations in environmental, climatic, and cultural conditions, however, without any variance in genotype.

1. 'VVA-1' propagates well by use of hardwood and softwood cuttings, as well as meristem cuttings in vitro.
2. 'VVA-1' serves well as rootstock that is compatible with other crops.
3. 'VVA-1' is resistant to frost.
4. 'VVA-1' exhibits a dwarf habit.
5. 'VVA-1' differs from the male parent by exhibiting long leaves, large, dark fruit and bearing very little fruit.
6. 'VVA-1' differs from the female parent by exhibiting wrinkled leaves, pubescent stems and short height.
7. 'VVA-1' exhibits white flowers.

BRIEF DESCRIPTION OF THE DRAWING

The photograph is an illustration of the new variety, VVA-1.

BOTANICAL DESCRIPTION OF THE PLANT

The following is a detailed botanical description of the new rootstock variety *Prunus* hybrid 'VVA-1'. Observations, measurements, values, and comparisons were collected in McMinnville, Oreg. from the inventor. The new variety was two (2) years old when described and was cultivated in a temperature variable environment. The foliage, flower and fruit exhibited by this cultivar are of no economic or commercial value, therefore comparisons and botanical descriptions of the foliage, fruit and flower are made for identification purposes only. Mature specimens, as well as bareroot specimens, were unavailable for photographing at the time this document was written. The color determinations are in accordance with The R.H.S. Colour Chart of The Royal Horticultural Society, London, England except where general color terms of ordinary dictionary significance are used.

Botanical classification: *Prunus tomentosa*×*Prunus cerasifera.*

Parentage: *Prunus* 'VVA-1' is an induced hybrid that resulted from crossing the following plants.

*Female parent.*—*Prunus tomentosa* (not patented).

*Male parent.*—*Prunus cerasifera* (not patented).

Type: Deciduous tree.

Use: 'VVA-1' serves well as rootstock for peach, apricot and plum crops.

Soil: Performs well in all soils and will tolerate heavy soils.

Light: Full sunlight.

Fruit bearing: No fruit observed on plants up to 3 years of age.

Crop time: 3 years is required for a rooted cutting to achieve finished product size that is ready to ship bareroot (rootstock 1 year and 2 more years with grafted scion).

Dimensions at crop time: 2.5 m. in height and 2 m. in width at 3 years.

Vigor: 50% of standard using *Prunus persica* as standard (peach seedling).

Habit: Dwarf and generally upright with some arching branches.

Hardiness: USDA Zone 4A.

Cold tolerance: Excellent.

Heat tolerance: Excellent.

Propagation: In winter 'VVA-1' is propagated by hardwood cuttings. In summer 'VVA-1' is propagated by softwood and meristem cuttings in vitro.

Rooting habit: Fine and fibrous initially. After 1 year roots become fleshy and thick.

Time to initiate roots: 1 year to develop roots on hardwood cuttings at 23° C. soil temperature and 5 months to develop roots on softwood and meristem cuttings in vitro at 22–25° Centrigrade air temperature.

Disease and insect resistance: Normal resistance to disease and insects.

Trunk:

*Trunk dimensions.*—4 cm. in diameter at 20 cm. above the soil at 3 years.

*Trunk bark surface.*—Glabrous surface.

*Trunk bark color.*—200C.

*Lenticels.*—Present but sparse.

*Lenticel dimensions on trunk.*—Up to 4 mm. in length and 1–2 mm. in width.

*Lenticel color.*—198B.

*Lenticel shape.*—Lens shaped.

Branches:

*Branch surface.*—Pubescent on young emerging branches. All other branches are glabrous.

*Branch color.*—200D.

*Internode length.*—5–7 cm. in length between nodes.

*Branching angle at emergence.*—70–80° and slightly bent.

*Branching habit.*—Freely branching.

*Pubescence.*—Present only on emerging young branches.

*Pubescence color.*—201C.

*Lenticels.*—Present but sparse on branches.

*Lenticel shape.*—Lens shaped.

*Lenticel color.*—198B.

*Lenticel dimensions.*—1–2 mm. in length and 1–2 mm. in width on branches.

*Lenticel number.*—*Approximately* 9 per inch on rootstocks over 1-year old.

Leaves:

*Arrangement.*—Alternate and whorled.

*Leaf length.*—4.5 cm. in length.

*Leaf width.*—3 cm. in width.

*Leaf shape.*—Oval.

*Leaf apex.*—Acuminate.

*Leaf base.*—Aequilateral.

*Leaf color* (*adaxial surface*).—135A.

*Leaf color* (*abaxial surface*).—134A.

*Leaf surface* (*adaxial*).—Undulate.

*Leaf surface* (*abaxial*).—Undulate.

*Leaf margins.*—Biserrate.

*Leaf division.*—Simple.

*Petiole dimensions.*—1.2 cm. in length and 1 mm. in width.

*Petiole color.*—135B.

*Petiole surface.*—Glabrous.

*Stipules.*—Absent.

*Leaf pubescence.*—Present on adaxial and abaxial surfaces.

*Color of pubescence.*—201C.

*Venation pattern.*—Pinnate.

*Vein color* (*adaxial and abaxial surfaces*).—135C.

*Leaf texture.*—Soft and wrinkled texture.

*Leaf strength.*—Moderate strength.

*Leaf appearance.*—Dull.

Fruit:

*Maturity.*—Requires 65–70 days to mature.

*Dates of picking.*—Not determined since the fruit has no commercial value.

*Production.*—Low. Produces a very small amount of fruit.

*Fruit form.*—Globose.

*Stem dimensions.*—1 cm. in length and 1–2 mm. in width.

*Stem color.*—136C.

*Skin color.*—201C.

*Skin surface.*—Pubescent.

*General color effect* (*with pubescence*).—59B.

*Lenticels.*—Absent.

*Flesh color.*—61A.

*Flesh texture.*—Moderately soft and juicy.

*Flavor.*—Highly acidic. Not recommended for consumption.

*Aroma.*—None.

*Seed number.*—One drupe.

*Seed shape.*—Oval.

*Seed color.*—164B.

*Seed dimensions.*—2.5 mm. in diameter and 3 mm. in length.

*Storage.*—Not determined because the fruit has no commercial value.

*Use.*—Fruit is not recommended for consumption and has no commercial value.

Flower:

*Arrangement.*—Solitary.

*Flower shape.*—Rotate.

*Bud dimensions.*—3 mm. in width and 3 mm. in length.

*Bud color.*—155C.

*Time of bloom.*—Flowers bloom when plant is 1 year and flowers last for 7–8 days.

*Flower diameter.*—2 cm. in diameter.

*Flower depth* (*throat*).—3 mm. in depth.

*Bloom quantity.*—Floriferous. 60–70 flowers per branch.

*Number of petals.*—Five petals in number.

*Fused or unfused.*—Petals are unfused.

*Petal shape.*—Variable from oval to slightly obovate.

*Petal margin.*—Entire.

*Flower color fully opened* (*upper and lower surfaces*).—155C.

*Dimensions of peduncle.*—0.8–1 cm. in length and 1 mm. in width.

*Color of peduncle.*—144D.

*Surface of peduncle.*—Pubescent.

*Color of pubescence.*—201C.

*Calyx dimensions.*—2.5–3 cm. in diameter and up to 2 mm. in length.

*Calyx surface.*—Pubescent.

*Color of pubescence.*—201C.

*Calyx color.*—144A.

*Number of sepals.*—Five sepals in number.

*Natural flowering season.*—Spring.

*Persistent or self-cleaning.*—Self-cleaning.

*Fragrance.*—None.

Reproductive organs:

*Stamen number.*—Polyandrous. 20–22 stamens and equal in length.

*Stamen color.*—155C.

*Anther.*—Single row with stamen attached at center of dorsal surface.

*Anther color.*—22A.

*Anther dimensions.*—Less than 1 mm. in length and less than 1 mm. in width.

*Amount of pollen.*—Small amount.

*Color of pollen.*—22A.

*Pistil.*—One in number.

*Pistil color.*—9A.

*Pistil dimensions.*—1–2 cm. in length and 0.50 mm. in width.

*Style color.*—9A.

*Style form.*—Elongate.

*Style dimensions.*—1 cm. in length and 0.50 mm. in width.

*Ovary dimensions.*—2 mm. in length and 2 mm. in width.

*Ovary color.*—155C.

*Ovary position.*—Superior.

I claim:

1. A new and distinct variety of *Prunus* plant named 'VVA-1', as herein described and illustrated.

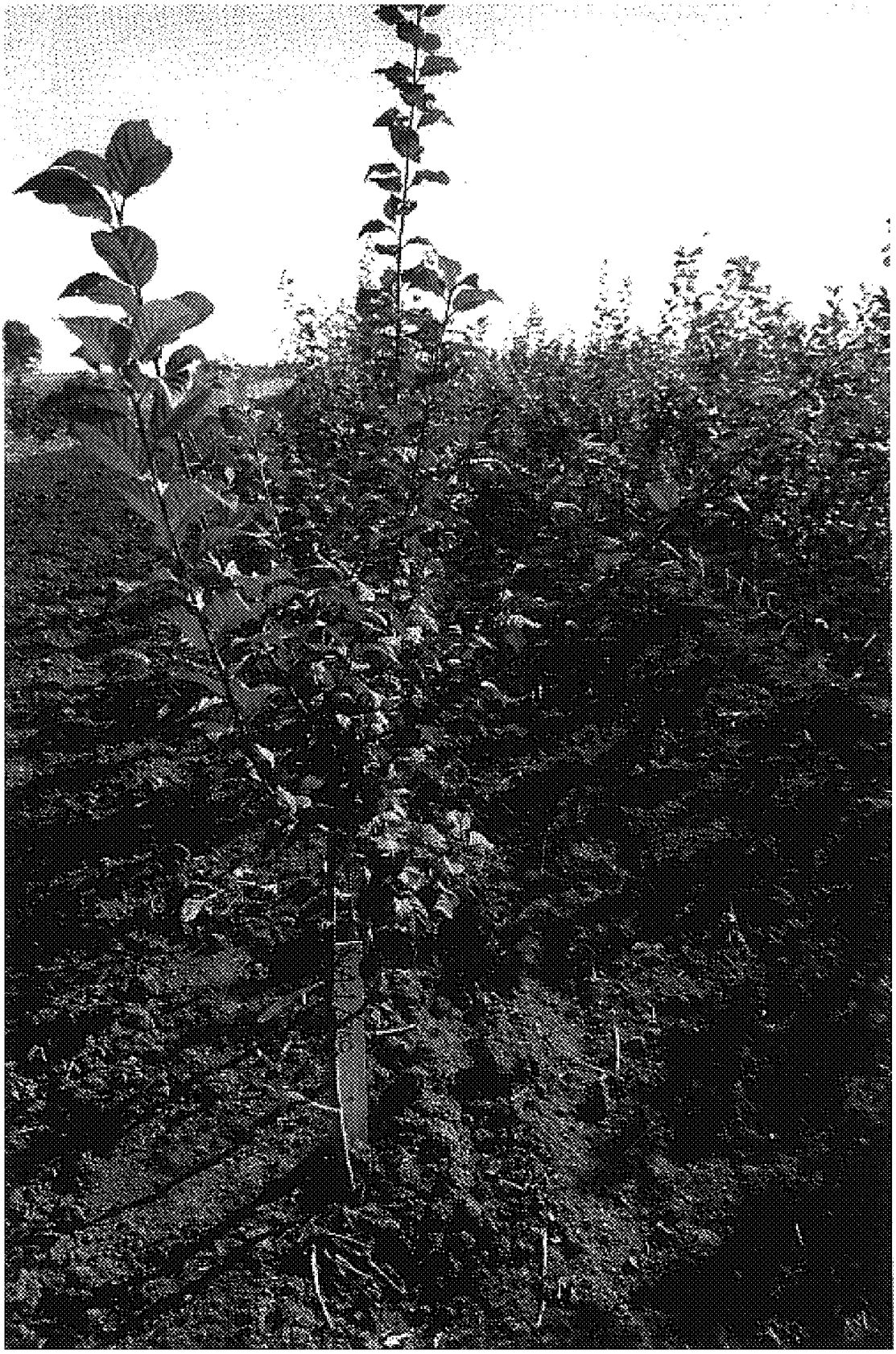

* * * * *